US006756408B2

(12) United States Patent
Uretsky (10) Patent No.: US 6,756,408 B2
(45) Date of Patent: Jun. 29, 2004

(54) METHODS AND MATERIALS FOR PROTECTING AGAINST MYOCARDIAL CELL DAMAGE RELATED TO CORONARY INTERVENTION BY REGIONAL BETA BLOCKER THERAPY

(75) Inventor: Barry F. Uretsky, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 30 days.

(21) Appl. No.: 10/201,639

(22) Filed: Jul. 22, 2002

(65) Prior Publication Data

US 2003/0045584 A1 Mar. 6, 2003

Related U.S. Application Data

(60) Provisional application No. 60/306,761, filed on Jul. 21, 2001.

(51) Int. Cl.[7] .............................................. A61K 31/135

(52) U.S. Cl. ...................................................... 514/652

(58) Field of Search ................................ 514/651, 652; 604/48, 500, 506, 507, 508, 509, 510

(56) References Cited

U.S. PATENT DOCUMENTS

| 5,320,604 A | 6/1994 | Walker et al. |
| 5,868,703 A | 2/1999 | Bertolero et al. |
| 6,087,394 A | 7/2000 | Duhaylongsod |

OTHER PUBLICATIONS

Pitt et al., "Effect of Propranolol on Regional Myocardial Blood Flow in Acute Ischaemia," Cardiovasc. Res., 4:176–179 (1970).
Maroko et al., "Factors Influencing Infarct Size Following Experimental Coronary Artery Occlusion," Circulation, 43:67–82 (1971).
Maroko et al., "Precordial S–T Segment Elevation Mapping: An Atraumatic Method for Assessing Alteration in the Extent of Myocardial Ischemic Injury," Am. J. Cardiol., 29:223–230 (1972)
Reimer et al., "Reduction by Propranolol of Myocardial Necrosis Following Temporary Coronary Occlusion in Dogs," Circ. Res., 33:353–363 (1973).
Becker et al., "Effect of Propranolol and Isoprenaline on Regional Left Ventricular Blood Flow in Experimental Myocardial Ischaemia," Cardiovasc. Res., 9:178–186 (1975).
Gold et al., "Regional Blockade with Intracoronary Propranolol," Circulation, 54(suppl II):II–173 (1976).
Kloner et al., "Distribution of Coronary Collateral Flow in Acute Myocardial Ischaemic Injury: Effect of Propranolol," Cardiovasc. Res., 10:81–96 (1976).
Reimer et al., "On the Nature of Protection by Propranolol Against Myocardial Necrosis after Temporary Coronary Occlusion in Dogs," Am. J. Cardiol., 37:520–527 (1976).

Shatney et al., "Effects of Allopurinol, Propranolol and Methylprednisolone on Infarct Size in Experimental Myocardial Infarction," Am. J. Cardiol., 37:572–579 (1976).
Rasmussen et al., "Infarct Size Reduction by Propranolol Before and after Coronary Ligation in Dogs," Circulation, 56:794–798 (1977).
Vatner et al., "Effects of Propranolol on Regional Myocardial Function, Electrograms, and Blood Flow in Conscious Dogs with Myocardial Ischemia," J. Clin. Invest., 60:353–360 (1977).
Jesmok et al., "Effects of Propranolol and Nitroglycerin Plus Methoxamine on Transmural Creatine Kinase Activity after Acute Coronary Occlusion," Am. J. Cardiol., 42:769–773 (1978).
Peter et al., "Reduction of Enzyme Levels by Propranolol after Acute Myocardial Infarction," Circulation, 57:1091–1095 (1978).
Miura et al., "The Effect of Delay in Propranolol Administration on Reduction of Myocardial Infarct Size after Experimental Coronary Artery Occlusion in Dogs," Circulation, 59:1148–1157 (1979).
O'Brien et al., "A Multiple Testing Procedure for Clinical Trials," Biometrics, 35:549–556 (1979).
Reynolds et al., "Effects of Propranolol on Myocardial Infarct Size With and Without Coronary Artery Reperfusion in the Dog," Cardiovasc. Res., 15:411–420 (1981).
Boyle et al., "Effect of Very Early Intervention with Metoprolol on Myocardial Infarct Size," Br. Heart J., 49:229–233 (1983).
Braunwald et al., "Role of Beta–adrenergic Blockade in the Therapy of Patients with Myocardial Infarction," Am. J. Med., 74:113–124 (1983).
Fox et al., "Myocardial Infarction in the Dog: Effects of Intravenous Propranolol," Am. J. Cardiol., 45:769–774 (1983).
Roberts et al., "Effect of Propranolol on Myocardial–infarct Size in a Randomized Blinded Multicenter Trial," N. Engl. J. Med., 311:218–25 (1984).
The International Collaborative Study Group, "Reduction of Infarct Size with the Early Use of Timolol in Acute Myocardial Infarction," N. Engl. J. Med., 310:9–15 (1984).
Oh et al., "Creatine Kinase Release after Successful Percutaneous Transluminal Coronary Angioplasty," Am. Heart J., 109:1225–1231 (1985).
Feldman et al., "Effect of Propranolol on Myocardial Ischemia Occurring During Acute Coronary Occlusion," Circulation, 73:727–733 (1986).

(List continued on next page.)

Primary Examiner—Raymond J. Henley, III
(74) Attorney, Agent, or Firm—Rogalskyj & Weyand, LLP (57) ABSTRACT

Disclosed is method for reducing myocardial cell damage during and/or after percutaneous coronary intervention in a subject's coronary artery. The method includes instilling a beta blocker directly into the subject's coronary artery prior to percutaneous coronary intervention. A kit for carrying out percutaneous coronary intervention is also disclosed. The kit includes a catheter and a beta blocker.

18 Claims, 4 Drawing Sheets

OTHER PUBLICATIONS

Zalewski et al., "Myocardial Protection During Transient Coronary Artery Occlusion in Man: Beneficial Effects of Regional Beta–adrenergic Blockade," *Circulation*, 73:734–739 (1986).

Pauletto et al., "Changes in Myoglobin, Creatine Kinase, and Creatine Kinase–MB after Percutaneous Transluminal Coronary Angioplasty for Stable Angina Pectoris," *Am. J. Cardiol.*, 59:999–1000 (1987).

Torr et al., "Effects on Infarct Size of Reperfusion and Pretreatment with –blockade and Calcium Antagonists," *Basic Res. Cardiol.*, 84:564–582 (1989).

Wappel et al., "Myocardial Salvage after Regional Beta–a-drenergic Blockade," *Am. Heart J.*, 117:37–42 (1989).

Klein et al., "Incidence and Clinical Significance of Transient Creatine Kinase Elevations and the Diagnosis of Non–Q Wave Myocardial Infarction Associated with Coronary Angioplasty," *J. Am. Coll. Cardiol.*, 17:621–626 (1991).

Labovitz et al., "Attenuation of Myocardial Ischemia During Coronary Occlusion by Ultrashort–acting Beta Adrenergic Blockade," *Am. Heart J.*, 121:1347–1352 (1991).

Abdelmeguid et al., "Defining the Appropriate Threshold of Creatine Kinase Elevation after Percutaneous Coronary Interventions," *Am. Heart J.*, 131:1097–1105 (1996).

Abdelmeguid et al., "Significance of Mild Transient Release of Creatine Kinase–MB Fraction after Percutaneous Coronary Interventions," *Circulation*, 94:1528–1536 (1996).

Kong et al., "Prognostic Implication of Creatine Kinase Elevation Following Elective Coronary Artery Interventions," *JAMA*, 277:461–466 (1997).

Wilson et al., "Prediction of Coronary Heart Disease Using Risk Factor Categories," *Circulation*, 97:1837–1847 (1998).

Simoons et al., "Minimal Myocardial Damage During Coronary Intervention Is Associated with Impaired Outcome," *Eur. Heart J.*, 20:1112–1119 (1999).

Sharma et al., "Cardioprotective Effect Prior –blocker Therapy in Reducing Creatine Kinase–MB Elevation after Coronary Intervention," *Circulation*, 102:106–172 (2000).

The Joint European Society of Cardiology/American College of Cardiology Committee, "Myocardial Infarction Redefined—A Consensus Document of The Joint European Society of Cardiology/American College of Cardiology Committee for the Redefinition of Myocardial Infarction," *Eur. Heart J.*, 21:1502–1513 (2000).

Topol et al., "Recognition of Importance of Embolization in Atherosclerotic Vascular Disease," *Circulation*, 101:570–580 (2000).

Blankenship et al., "Effect of Glycoprotein IIb/IIIa Receptor Inhibition on Angiographic Complications During Percutaneous Coronary Intervention in the ESPRIT Trial," *J. Am. Coll. Cardiol.*, 38:653–658 (2001).

Blankenship et al. for IMPACT II Investigators, "Effect of Eptifibatide on Agiographic Complications During Percutaneous Coronary Intervention in the Impact– (Integrilin to Minimize Platelet Aggregation and Coronary Thrombosis) II Trial," *Am. J. Cardiol.*, 88:969–973 (2001).

Ellis et al., "Beta–Blockers Before Percutaneous Coronary Intervention Do Not Attenuate Postprocedural Creatine Kinase Isoenzyme Rise," *Circulation*, 104:2685–2688 (2001).

Akkerhuis et al., "Minor Myocardial Damage and Prognosis: Are Spontaneous and Percutaneous Coronary Intervention–Related Events Different?" *Circulation*, 105:554–556 (2002).

METHODS AND MATERIALS FOR PROTECTING AGAINST MYOCARDIAL CELL DAMAGE RELATED TO CORONARY INTERVENTION BY REGIONAL BETA BLOCKER THERAPY

The present application claims the benefit of U.S. Provisional Patent Application Serial No. 60/306,761, filed Jul. 21, 2001, which is hereby incorporated by reference.

FIELD OF THE INVENTION

The subject invention relates, generally, to methods and materials for protecting a subject against myocardial cell damage and, more particularly, for protecting a subject against myocardial cell damage resulting from coronary intervention.

BACKGROUND OF THE INVENTION

Percutaneous coronary intervention ("PCI") is an important treatment for coronary artery disease and other forms of atherosclerosis obstruction of the coronary arteries. However, myocardial necrosis (infarction) during PCI may occur in almost half of otherwise successful PCI (Klein et al., "Incidence and Clinical Significance of Transient Creatine Kinase Elevations and the Diagnosis of Non-Q Wave Myocardial Infarction Associated with Coronary Angioplasty," *J. Am. Coll. Cardiol.*, 17:621–626 (1991) ("Klein"); Oh et al., "Creatine Kinase Release after Successful Percutaneous Transluminal Coronary Angioplasty," *Am. Heart J.*, 109:1225–1231 (1985) ("Oh"); and Pauletto et al., "Changes in Myoglobin, Creatine Kinase, and Creatine Kinase-MB after Percutaneous Transluminal Coronary Angioplasty for Stable Angina Pectoris," *Am. J. Cardiol.*, 59: 999–1000 (1987)) and is associated with an increased incidence of late adverse outcomes, particularly death, even with minor elevations in biochemical markers (Simoons et al., "Minimal myocardial damage during coronary intervention is associated with impaired outcome," *Eur. Heart J.*, 20:1112–1119 (1999) ("Simoons"); Kong et al., "Prognostic implication of creatine kinase elevation following elective coronary artery interventions," *JAMA*, 277:461–466 (1997); Abdelmeguid et al., "Significance of Mild Transient Release of Creatine Kinase-MB Fraction after Percutaneous Coronary Interventions," *Circulation*, 94:1528–1536 (1996); and Akkerhuis et al., "Minor Myocardial Damage and Prognosis: Are Spontaneous and Percutaneous Coronary Intervention—Related Events Different?" *Circulation*, 105:554–556 (2002)). These biochemical markers include the enzyme creatine kinase ("CK"), the myocardial specific enzyme CKMB, and the myocardial cell protein troponin I and troponin T, and an increase in these markers after PCI is associated with a worsened prognosis.

The causes of myocardial enzyme elevation after otherwise successful PCI are multiple and are believed to include the development of mechanical complications such as slow flow, side branch occlusion, transient major vessel closure, or prolonged coronary spasm (Klein and Oh). In the majority of cases, however, enzyme release occurs without any apparent mechanical complication. In this setting, the most likely cause is microembolization (Topol et al., "Recognition of Importance of Embolization in Atherosclerotic Vascular Disease," *Circulation*, 101:570–580 (2000)).

In an effort to reduce post-PCI complications, various compounds can be administered to the subject. These include glycoprotein IIb/IIIa receptor antagonists, aspirin, and heparin. However, these compounds have not proven to be wholly effective in reducing post-PCI myocardial necrosis and other forms of post-PCI cell myocardial cell damage.

Accordingly, there exists a need for methods of protecting against the incidence of myocardial necrosis and other forms of myocardial cell damage during or subsequent to PCI. The present invention is directed, in part, to meeting this need.

SUMMARY OF THE INVENTION

The present invention relates to a method for reducing myocardial cell damage during and/or after percutaneous coronary intervention in a subject's coronary artery. The method includes instilling a beta blocker directly into the subject's coronary artery prior to percutaneous coronary intervention.

The present invention also relates to a kit for carrying out percutaneous coronary intervention. The kit comprises a catheter and a beta blocker.

DETAILED DESCRIPTION OF THE INVENTION

The present invention relates to a method for reducing myocardial cell damage during and/or after percutaneous coronary intervention in a subject's coronary artery.

Suitable subjects include mammals, such as humans, and particularly humans who suffer from coronary artery disease and/or other forms of atherosclerosis obstruction of the coronary arteries. The method of the present invention can be practiced on subjects who, in addition to benefitting from a reduction in myocardial necrosis, might benefit from some other potential effects of intracoronary administration of beta blockers. Examples of such subjects include those in need of improving tolerance to stress (e.g., pacing, which increases myocardial oxygen demand) and/or those in need of improving tolerance to ischemia (e.g., ischemia produced by a decrease in blood flow by balloon occlusion of a coronary artery during angioplasty). Alternatively, the method can be practiced on subjects who would derive no significant additional benefit (i.e., in addition to the reduction of myocardial necrosis) from some or all of these (or other) potential additional effects of intracoronary administration of beta blockers.

As used herein, "myocardial cell damage" is meant to include myocardial necrosis, myocardial infarction, and all other forms of damage to heart tissue, as evidenced, for example, by the release of biochemical markers associated with myocardial cell damage, such as creatine kinase, myocardial specific enzyme CKMB, myocardial cell protein troponin I, and/or myocardial cell protein troponin T. As used herein, "reducing" is meant to refer to any measurable or otherwise observable decrease (e.g., at least a 1% decrease, at least a 5% decrease, at least a 10% decrease, at least a 20% decrease, etc.) in the incidence and/or degree of myocardial necrosis or other forms of myocardial cell damage, as evidenced, for example, by a measurable decrease (relative to a historical or other suitable control) in the rate of adverse clinical events (e.g., death, myocardial infarction, etc.) and/or (ii) a measurable decrease (relative to a historical or other suitable control) in the amount of one or more biochemical markers associated with myocardial cell damage (e.g., one or more of creatine kinase, myocardial specific enzyme CKMB, myocardial cell protein troponin I, and myocardial cell protein troponin T) released during and/or after PCI. It will be appreciated that, as used herein, "reducing" is also meant to include a total prevention in the incidence and/or degree of myocardial necrosis or other forms of myocardial cell damage during and/or after PCI.

The myocardial cell damage to be reduced by the practice of the method of the present invention can be attributable to any mechanism. Illustratively, the myocardial cell damage to be reduced can be "ischemia-induced myocardial cell damage" or it can be "non-ischemia-induced myocardial cell damage". In this regard, "ischemia-induced myocardial cell damage" is meant to refer to myocardial cell damage which is caused, directly or indirectly, by ischemia (such as that resulting from balloon occlusion of the coronary artery during PCI) while "non-ischemia-induced myocardial cell damage" is meant to refer to myocardial cell damage which is not caused, directly or indirectly, by ischemia (such as that resulting from balloon occlusion of the coronary artery during PCI).

"Percutaneous coronary intervention", as used herein, is meant to include any procedure which is carried out on a coronary artery, which is carried out percutaneously, and which is designed to alleviate the cause or symptoms of coronary artery disease and other forms of atherosclerosis obstruction of the coronary arteries. Illustratively, "percutaneous coronary intervention" is meant to include, for example, stenting, atherectomy, and angioplasty, such as balloon angioplasty. The "percutaneous coronary intervention" can be one which involves temporarily occluding the coronary artery (e.g., balloon angioplasty), or it can be one which does not involve temporarily occluding the coronary artery (e.g., non-balloon angioplasty procedures, stenting procedures that do not involve balloon angioplasty, etc.). Methods for carrying these and other percutaneous coronary intervention procedures are well known to those skilled in the art and are described, for example, in Topol, *Textbook of Interventional Cardiology,* 3rd ed., Philadelphia, Pa.: W. B. Saunders (1999) ("Topol"), which is hereby incorporated by reference; in Ellis et al., *Strategic Approaches in Coronary Intervention,* 2nd ed., Philadelphia, Pa.: Lippincott Williams & Wilkins (2000) ("Ellis"), which is hereby incorporated by reference; and/or in Safian et al., *The Manual of Interventional Cardiology,* 3rd ed., Royal Oak, Mich.: Physicians' Press (2001) ("Safian"), which is hereby incorporated by reference.

"Coronary artery", as used herein, is meant to refer to any blood vessel which supplies blood to heart tissue of the subject and is meant to include native coronary arteries as well as those which have been grafted into the subject, for example, in an earlier coronary artery bypass procedure.

As indicated above, the method of the present invention involves instilling a beta blocker directly into the subject's coronary artery prior to percutaneous coronary intervention.

As used herein, "beta blockers" are meant to include any compound which is a competitive antagonist of a beta-adrenergic receptor. "Beta blockers", as used herein are meant to include compounds which, in addition to being competitive antagonists of a beta-adrenergic receptor, are also competitive antagonists of other receptors. Thus, for example, a compound which is both a competitive antagonist of a beta-adrenergic receptor and of an alpha-adrenergic receptor, is, for the purposes of the present invention, intended to be deemed to be a "beta blocker". Suitable beta blockers include, for example, propranolol, sotalol, timolol, carteolol, carvedilol, nadolol, betaxolol, penbutolol, metoprolol, labetalol, acebutolol, atenolol, pindolol, bisoprolol, acebutolol, oxprenolol, esmolol; alternative pharmaceutically acceptable salts, esters, hydrates, complexes, etc. of these compounds; and/or compounds which are competitive antagonists of a beta-adrenergic receptor to a degree which is at least about 25% (e.g., at least about 50%, at least about 75%, at least about 100%) that of propranolol. Combinations of beta blockers can also be employed, and the term "beta blocker" is meant to include such combinations of beta blockers.

The beta blocker can be instilled directly into the subject's coronary artery in any suitable way. Typically, the subject's coronary artery into which the beta blocker is to be instilled and on which the PCI procedure is to be performed will contain a blockage, such as a stenosis or some other form of complete or partial blockage which causes reduced blood flow through the coronary artery. Thus, in most situations, the beta blocker can be delivered conveniently to the coronary artery via a catheter which is percutaneously inserted into the subject and which is threaded through the subject's blood vessels to the target coronary artery. The catheter used to deliver the beta blocker can be the same catheter through which PCI is to be performed, or it can be a different catheter (e.g., a different catheter which is percutaneously inserted into the subject via the same or a different cutaneous incision and/or which is threaded through the subject's blood vessels to the target coronary artery via the same or a different route). Still alternatively, the use of catheter can be dispensed with altogether, for example, where it is possible to inject the beta blocker directly into the coronary artery, for example, through the subject's chest with a syringe.

For example, in the case where the coronary artery contains a blockage (e.g., a stenosis), instilling can be carried out by delivering the beta blocker directly to the coronary artery at the site of the blockage or distal to the blockage or both. In addition to being delivered directly to the coronary artery at the blockage or distal to the blockage or both, the beta blocker can also be delivered to one or more sites proximal to the blockage. Alternatively, the beta blocker can be instilled in such a way that it is delivered directly to the coronary artery at the blockage and/or distal to the blockage but not proximal to the blockage. In the case where the beta blocker is delivered via a catheter (e.g., a dilatation catheter, an over-the-wire angioplasty balloon catheter, an infusion catheter, a rapid exchange or monorail catheter, etc.) to the coronary artery, delivery at the blockage or distal to the blockage or both can be effectively carried out by positioning the catheter's distal tip across the stenosis or blockage. Alternatively, the catheter's distal tip can be placed near but distal to the stenosis or other blockage, such as within 50 (e.g., within 20, within 10, etc.) blood vessel diameters of the stenosis or other blockage; and the beta blocker can be delivered to such a position distal to the blockage. It will be appreciated that the catheter tip can be maintained stationary while the beta blocker is being delivered. Alternatively, the catheter tip can be moved while the beta blocker is being delivered, for example, in a proximal direction, from a position which is initially distal to the blockage; to or through the blockage; and, if desired, to a position which is proximal to the blockage.

As indicated above, the beta blocker is instilled directly into the subject's coronary artery at a time prior to percutaneous coronary intervention. For example, delivery of the beta blocker can be carried out immediately (e.g., within about 1 hour, such as within about 30 minutes, within about 15 minutes, and/or within about 5 minutes) prior to percutaneous coronary intervention. Optionally, delivery of the beta blocker directly to the coronary artery can be continued during all or part of the percutaneous coronary intervention procedure and/or subsequent to completion of such procedure; or delivery of the beta blocker directly to the coronary artery can be stopped prior to the commencement of the percutaneous coronary intervention procedure and not subsequently re-commenced. In all cases, delivery of the beta blocker can be continuous or it can be effected in one bolus or in a plurality of boli.

Prior to, during, and/or after the beta blocker is delivered directly to the coronary artery, the same beta blocker(s) or one or more different beta blockers can be administered systemically (i.e., not delivered directly to the coronary artery).

Still additionally or alternatively, prior to, during, and/or after the beta blocker is delivered directly to the coronary artery, other compounds conventionally used to prevent or reduce myocardial necrosis can be administered to the subject by any suitable route. Such other compounds include, for example, glycoprotein IIb/IIIa receptor antagonists, such as abciximab and eptifibatide and other compounds that are believed to decrease the incidence of PCI-related myocardial necrosis by inhibiting platelet aggregation, thus decreasing platelet microemboli (which prevent oxygen-carrying red blood cells from arriving at areas of the myocardium, thus producing islands of myocardial necrosis); aspirin; and heparin and other compounds which decrease the propensity of blood clotting caused by activation of blood and tissue proteins that stimulate clotting (which blood and tissue proteins are commonly released during PCI as the result of trauma due to blood vessel manipulation).

Typically, the beta blocker is instilled directly into the subject's coronary artery under conditions which are effective to reduce myocardial cell damage during and/or after percutaneous coronary intervention, for example, as evidenced by an inhibition in the release of enzyme creatine kinase, myocardial specific enzyme CKMB, myocardial cell protein troponin I, myocardial cell protein troponin T, or combinations thereof. Effective conditions can be readily ascertained by those skilled in the art with reference to the above discussion and the examples which follow.

For example, the beta blocker used in the method of the present invention can be administered alone or in combination with suitable pharmaceutical carriers or diluents. Diluent or carrier ingredients used in the beta blocker formulation should be selected so that they do not diminish the desired effects of the beta blocker. The beta blocker formulation may be made up in any suitable form appropriate for the administration directly to the coronary artery. Examples of suitable dosage forms include solutions, and the like. Alternatively, the beta blocker can be provided in the form of a sterile solid composition which can be dissolved in a sterile injectable medium immediately before use. Suitable beta blocker formulations include those which contain other excipients known in the art, such as the ones further discussed below.

Illustratively, fluid unit dosage forms of beta blockers suitable for instillation directly into a subject's coronary artery can be prepared utilizing a beta blocker (or two or more beta blockers) and a sterile vehicle, saline being preferred. The beta blocker, depending on the vehicle and concentration used, can be dissolved in the vehicle in any suitable concentration. In preparing solutions, the beta blocker can be dissolved in saline and filter sterilized before filling into a suitable vial or ampule and sealing. Advantageously, adjuvants, such as preservatives and buffering agents, can be dissolved in the vehicle. To enhance the stability, the composition can be freeze-dried. The dry lyophilized powder can then sealed in the vial, and an accompanying vial of water for injection can be supplied to reconstitute the liquid prior to use.

In addition to the above-described excipients etc., the beta blocker formulation can also (i.e., in addition to the beta blocker) contain other active pharmaceutical agents, such as those discussed above.

Suitable concentrations of beta blocker in the beta blocker formulation include from about 0.1 mg/ml to about 10 mg/ml, such as from about 0.5 mg/ml to about 2 mg/ml and/or about 1 mg/ml.

Suitable dosages can be ascertained by standard methods, such as by establishing dose-response curves in laboratory animal models or in clinical trials. Illustratively, suitable dosages of beta blocker (administered in a single bolus or over time) include from about 1 $\mu$g/kg (of the subject's body weight) to about 150 $\mu$g/kg, such as from about 3 $\mu$g/kg to about 75 $\mu$g/kg, from about 5 $\mu$g/kg to about 50 $\mu$g/kg, from about 10 $\mu$g/kg to about 25 $\mu$g/kg, and/or about 15 $\mu$g/kg.

Once the beta blocker has been delivered directly to the coronary artery, percutaneous coronary intervention can be carried out by any conventional procedure. Examples of percutaneous coronary intervention procedures contemplated for use in conjunction with the method of the present invention include stenting, atherectomy, and angioplasty, such as balloon angioplasty. The percutaneous coronary intervention procedure can be one which involves temporarily occluding the coronary artery (e.g., balloon angioplasty), or it can be one which does not involve temporarily occluding the coronary artery (e.g., non-balloon angioplasty procedures, stenting procedures that do not involve balloon angioplasty, etc.). Methods for carrying these and other percutaneous coronary intervention procedures are well known to those skilled in the art and are described, for, example, in Topol, Ellis, and/or Safian, which are hereby incorporated by reference.

The present invention, in another aspect thereof, relates to a kit for carrying out percutaneous coronary intervention. The kit includes a catheter and a beta blocker. The beta blocker can be provided in any of the formulations discussed above and in an amount needed to carry our a single percutaneous coronary intervention, such as from about 30 $\mu$g to about 30 mg, from about 100 $\mu$g to about 10 mg, from about 450 $\mu$g to about 4 mg, from about 450 $\mu$g to about 3 mg, from about 150 $\mu$g to about 4 mg, and/or from about 150 $\mu$g to about 3 mg. Alternatively, the kit can contain more than one catheter and a plurality of separate containers, each containing sterilized beta blocker formulations in an amount needed to carry our a single percutaneous coronary intervention. Suitable catheters for inclusion with the kit include dilatation catheters, over-the-wire angioplasty balloon catheters, infusion catheters, rapid exchange or monorail catheters, and the like. Suitable beta blockers include propranolol as well as those which have been described above in connection with the method of the present invention. Illustratively, a kit of the present invention can include an over-the-wire angioplasty balloon catheter and propranolol, where the propranolol is present in a solution at a concentration of about 0.1 to about 10 mg/ml and where the propranolol is present in an amount of from about 150 μg to about 4 mg.

The present invention is further illustrated by the following examples.

EXAMPLES

Example 1
Distal Myocardial Protection During Percutaneous Coronary Intervention with an Intracoronary Beta Blocker—Materials and Methods Study population: This study was a randomized, double-blind, placebo-controlled trial. Patients with coronary artery disease undergoing PCI were considered for inclusion. Patients on chronic beta blockers were included. Exclusion criteria included myocardial infarction ("MI") within 24 h or recent MI with elevation of CK or CKMB at time of randomization (a normal CK and CKMB and elevated troponin T allowed inclusion); cardiogenic shock; systolic blood pressure<100 mm Hg; heart rate<50/min; NYHA class III or IV heart failure; severe left ventricular dysfunction (ejection fraction<30%); severe renal insufficiency (creatinine>3.0 mg/dl); allergy to propranolol; or second planned intervention within 30 days. Patients with chronic obstructive pulmonary disease ("COPD") were not specifically excluded.

Study protocol: Before initiation of PCI, all patients were pretreated with aspirin and received weight-adjusted heparin, with a target activated clotting time of >300 seconds in the absence of a glycoprotein IIb/IIIa ("GP IIb/IIIa") inhibitor and 200–300 seconds with a GP IIb/IIIa inhibitor, which was allowed but not mandated.

Patients were randomized in a 1:1 ratio to receive either placebo or propranolol. The randomization allocation code was generated using complete block design. Randomization was performed after coronary angiography confirmed the need for PCI. In patients with a total occlusion, the lesion was crossed with a guide wire before randomization.

Study drug kits were packaged by hospital pharmacy to be indistinguishable from each other with a concentration of 1 mg/ml; the identity of the injectate (i.e., propranolol or placebo) was not known to the investigators or to the patients. Propranolol at a dose of 15 μg/kg (Zalewski et al., "Myocardial Protection During Transient Coronary Artery Occlusion in Man: Beneficial Effects of Regional Beta-Adrenergic Blockade," *Circulation*, 73:734–739 (1986), which is hereby incorporated by reference) or 0.9% NaCl (placebo) was injected into the coronary artery through the dilatation catheter whose distal tip was positioned across the stenosis or stenoses (if more than one site underwent PCI). The study drug was thus delivered directly into the myocardial region supplied by the stenotic coronary artery undergoing PCI. Balloon inflation was performed after the IC injection of propranolol or placebo. Blood samples were taken prior to PCI, immediately after PCI, and every 8 h for 24 h to assay CK and CKMB. Blood samples were taken at 16 h for troponin T analysis. Additional blood levels were obtained when any patient experienced possible ischemic symptoms. The 30-day contact was made by clinic visit or telephone interview.

Study endpoints: The primary endpoint was the incidence of post-procedural elevation of CKMB above the upper limit of normal ("ULN"). The "threshold" for the development of an excess in adverse events relative to the level of CKMB appears to be a continuous function beginning with any elevation of CKMB or troponin T with the frequency of long-term adverse events, particular death, increasing with the level of enzyme rise (Simoons, which is hereby incorporated by reference). Secondary endpoints included (1) incidence of post-procedure total CK elevation, (2) incidence of troponin T elevation (in those patients with normal baseline values), (3) median peak values of CK, CKMB, and troponin T, (4) rescue therapy with GP IIb/IIIa inhibitors, and (5) combination of death from any cause, myocardial necrosis, recurrent MI within 30 days, or severe myocardial ischemia requiring urgent coronary-artery bypass surgery or target lesion revascularisation ("TLR") within 30 days of intervention ("MACE").

Definitions: Evidence of myocardial necrosis was defined as an increase above the ULN in total CK, CKMB, or troponin T. Recurrent MI within the first 30 days was defined as an acute coronary syndrome with or without electrocardiographic changes and elevation of a cardiac marker (The Joint European Society of Cardiology/American College of Cardiology Committee, "Myocardial Infarction Redefined—A Consensus Document of The Joint European Society of Cardiology/American College of Cardiology Committee for the Redefinition of Myocardial Infarction," *Eur. Heart J.*, 21:1502–1513 (2000), which is hereby incorporated by reference). Urgent target lesion revascularisation included any coronary artery bypass graft surgery or a second PCI on the original target lesion performed for recurrent myocardial ischemia. Successful PCI was defined as post-procedure residual stenosis at the target lesion<30% of reference vessel diameter without major adverse outcome (death, Q wave MI, emergent CABG). Major bleeding was defined as bleeding requiring transfusion, surgery, prolongation of hospital stay, or >8% drop in hematocrit after PCI. Rescue GP IIb/IIIa use was defined as drug given after the guide wire passage during PCI. Risk factors utilized standardized definitions (Wilson et al., "Prediction of Coronary Heart Disease Using Risk Factor Categories," *Circulation*, 97:1837–1847 (1998), which is hereby incorporated by reference). Mechanical complications included dissection, abrupt or threatened closure of PCI vessel, transient or permanent side branch closure, angiographic embolization, development of new intracoronary angiographic thrombus, decrease in flow ("slow flow") or stoppage of flow ("no flow") in the epicardial PCI vessel in the setting of an adequately opened lesion.

Data management and statistical analysis: Data were collected prospectively on case-report forms. The investigators and study coordinators were blinded to the treatment assignment until after the database was sealed following entry of all data. All analyses were performed using the intention-to-treat principle. Continuous variables were summarized by mean±standard deviation and compared between groups by the two-tailed t test. Categorical variables were summarized by percentages and compared using the chi-square statistic or Fisher exact test wherever appropriate. Treatment effects by subgroups are reported as relative risks ("RRs") with 95% confidence intervals ("CIs"). Multivariate logistic regression analysis was used to determine the independent predictors of the primary endpoint. Methods for survival analysis were used for the 30-day MACE. Time to first occurrence of the composite end point is shown by Kaplan-Meier survival curves.

Sample-size determination and interim analyses: A sample size of 150 patients, with 75 patients in each group, was required to have 80% power based on the assumption of an incidence of postprocedural CKMB increase of 8% and 24% in the 2 groups (Simoons, which is hereby incorporated by reference). Since no published reports were available for the expected incidence of the primary end point in the propranolol group, two blinded interim analyses at 50 and 100 samples were planned to determine if there was a trend worthy of continuing the trial. Using the O'Brien-Fleming multiple testing method, a significant difference at the final analysis at 150 patients was considered to be a p value of <0.045 (O'Brien et al., "A Multiple Testing Procedure for Clinical Trials," *Biometrics,* 35:549–556 (1979), which is hereby incorporated by reference).

Interim analyses: Interim analysis after the first 50 patients revealed that there was a difference between the 2 groups in CKMB elevation after PCI (19% vs. 45%, p=0.04). The second interim analysis after 100 patients showed there was a greater statistical difference (p=0.009), 18% and 42% respectively. The incidence of MACE, other than myocardial necrosis (i.e., death, recurrent MI, and urgent TLR), over the first 30 days was very low, and there was no significant difference between the two groups in these end points at the time of first and second interim analyses. It was, therefore, decided to continue the double blind study until the original sample size was reached in order to increase the robustness of the final results.

Example 2

Distal Myocardial Protection During Percutaneous Coronary Intervention with an Intracoronary Beta Blocker—Results From Jul. 18, 2000, to May 30, 2002, 150 patients were enrolled with the last follow-up on Jul. 1, 2002. Baseline demographic and angiographic characteristics between groups were similar, as shown in Tables 1 and 2. There was no change in the heart rate or blood pressure after IC injection of propranolol or placebo. There were no adverse systemic effects after IC injection in either group, including respiratory difficulties in 5 patients with a history of COPD or asthma.

TABLE 1

Baseline clinical characteristics (% of patients unless otherwise stated).

| Characteristics | Propranolol (n = 75) | Placebo (n = 75) |
|---|---|---|
| Age (yr) | 58 ± 12 | 58 ± 12 |
| Male sex | 56 | 65 |
| Race | | |
| Caucasian | 64 | 73 |
| African-American | 27 | 20 |
| Other | 9 | 7 |
| Weight (kg) | 84 ± 17 | 89 ± 21 |
| Diabetes mellitus | 36 | 49 |
| Current smoking | 40 | 41 |
| Hypercholesterolemia | 59 | 64 |
| Hypertension | 80 | 75 |
| History of MI | 44 | 43 |
| Family history of CAD | 44 | 52 |
| Previous PCI | 44 | 37 |
| Previous CABG | 12 | 24 |

TABLE 1-continued

Baseline clinical characteristics (% of patients unless otherwise stated).

| Characteristics | Propranolol (n = 75) | Placebo (n = 75) |
|---|---|---|
| Clinical presentation | | |
| Post MI | 16 | 9 |
| Unstable angina | 56 | 71 |
| Stable angina | 28 | 20 |

CABG = coronary artery bypass surgery;
CAD = coronary artery disease;
MI = myocardial infarction;
PCI = percutaneous coronary intervention

TABLE 2

Procedural and angiographic characteristics (% of patients unless otherwise stated).

| Characteristics | Propranolol (n = 75) | Placebo (n = 75) |
|---|---|---|
| Systolic BP, baseline (mmHg) | 139 ± 25 | 143 ± 28 |
| Systolic BP, post drug * (mmHg) | 137 ± 23 | 142 ± 28 |
| Heart rate, baseline (beats/min) | 67 ± 11 | 67 ± 10 |
| Heart rate, post drug * (beats/min) | 66 ± 11 | 66 ± 10 |
| Vessel ** | | |
| LAD | 28 | 31 |
| RCA | 48 | 38 |
| LCX | 20 | 24 |
| SVG | 1 | 5 |
| Other | 3 | 2 |
| Nature of lesion | | |
| De novo | 77 | 87 |
| Restenosis | 23 | 13 |
| Thrombus at baseline | 9 | 8 |
| Type of lesion | | |
| A/B1 | 54 | 50 |
| B2/C | 46 | 50 |
| Pre-/post-procedural TIMI flow | | |
| 0/1 | 7/0 | 9/1 |
| 2 | 1/0 | 2/0 |
| 3 | 91/100 | 89/99 |
| Type of procedure | | |
| PTCA only | 20 | 24 |
| Stent ± PTCA | 80 | 75 |
| Stent ± RA | 0 | 1 |
| Multivessel intervention | 8 | 7 |
| Procedural success | 100 | 99 |
| Prophylactic GP IIb/IIIa use | 33 | 23 |
| Patients with ≧1 angiographic complications | 23 | 24 |
| Coronary dissection | 15 | 13 |
| Transient/permanent side-branch closure | 3 | 5 |
| Threatened/abrupt closure | 3 | 3 |
| Macroembolization | 1 | 1 |
| New thrombus | 1 | 1 |
| Slow flow/no reflow | 9 | 5 |

LAD = left anterior descending;
LCX = circumflex;
RCA = right coronary artery;
SVG = saphenous vein graft;
TIMI = Thrombolysis In Myocardial Infarction grading system;
PTCA = percutaneous transluminal coronary angioplasty;
RA = rotational atherectomy.
* represents largest change after drug administration.
** indicates that the number of vessels is greater than the number of patients as some patients had PCI on more than one vessel.

Figure 1:
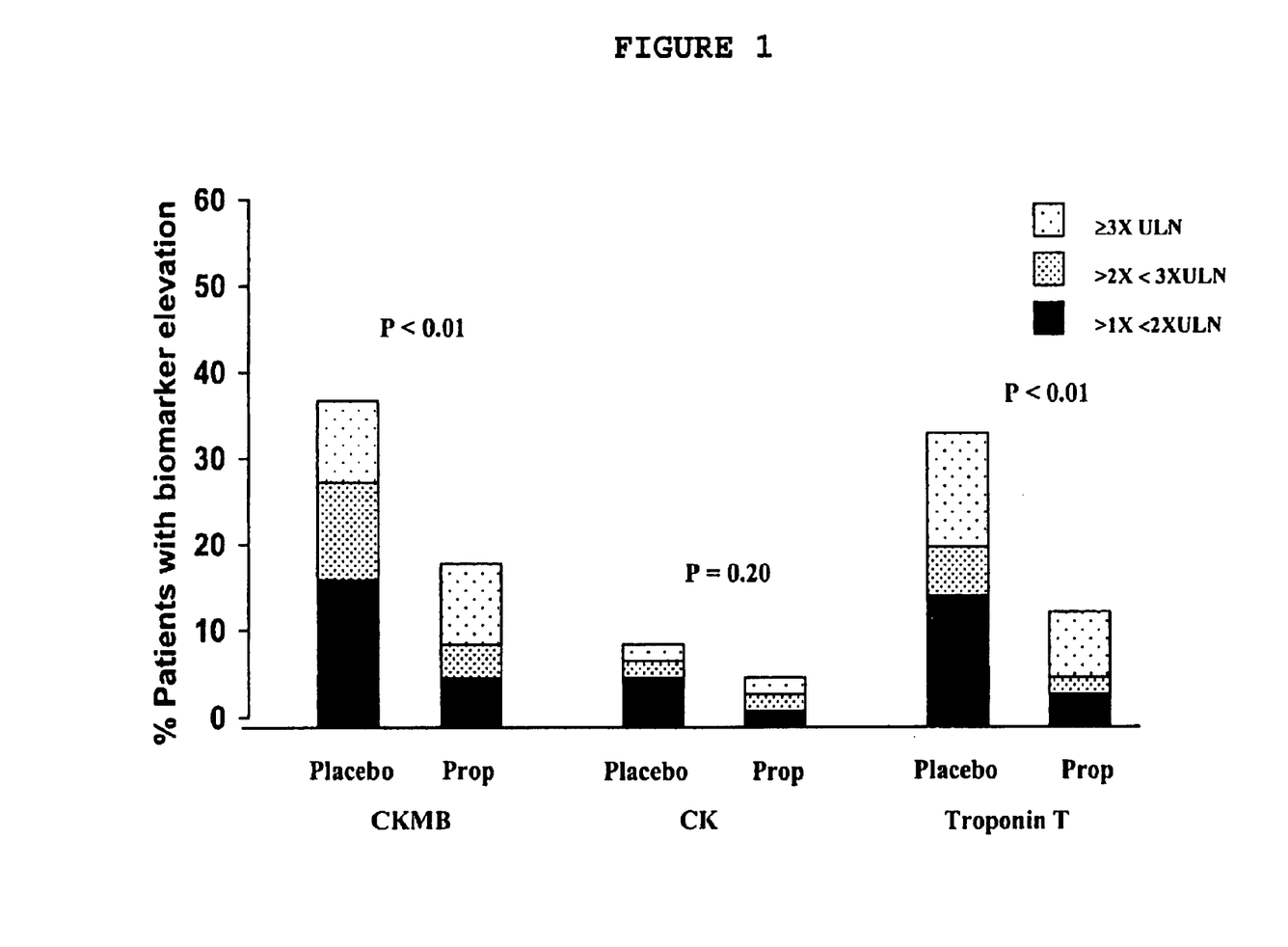
FIG. 1 is a bar graph showing the effect of a beta blocker, used in accordance with a method of the present invention, on biomarker elevation.
Figure 2:
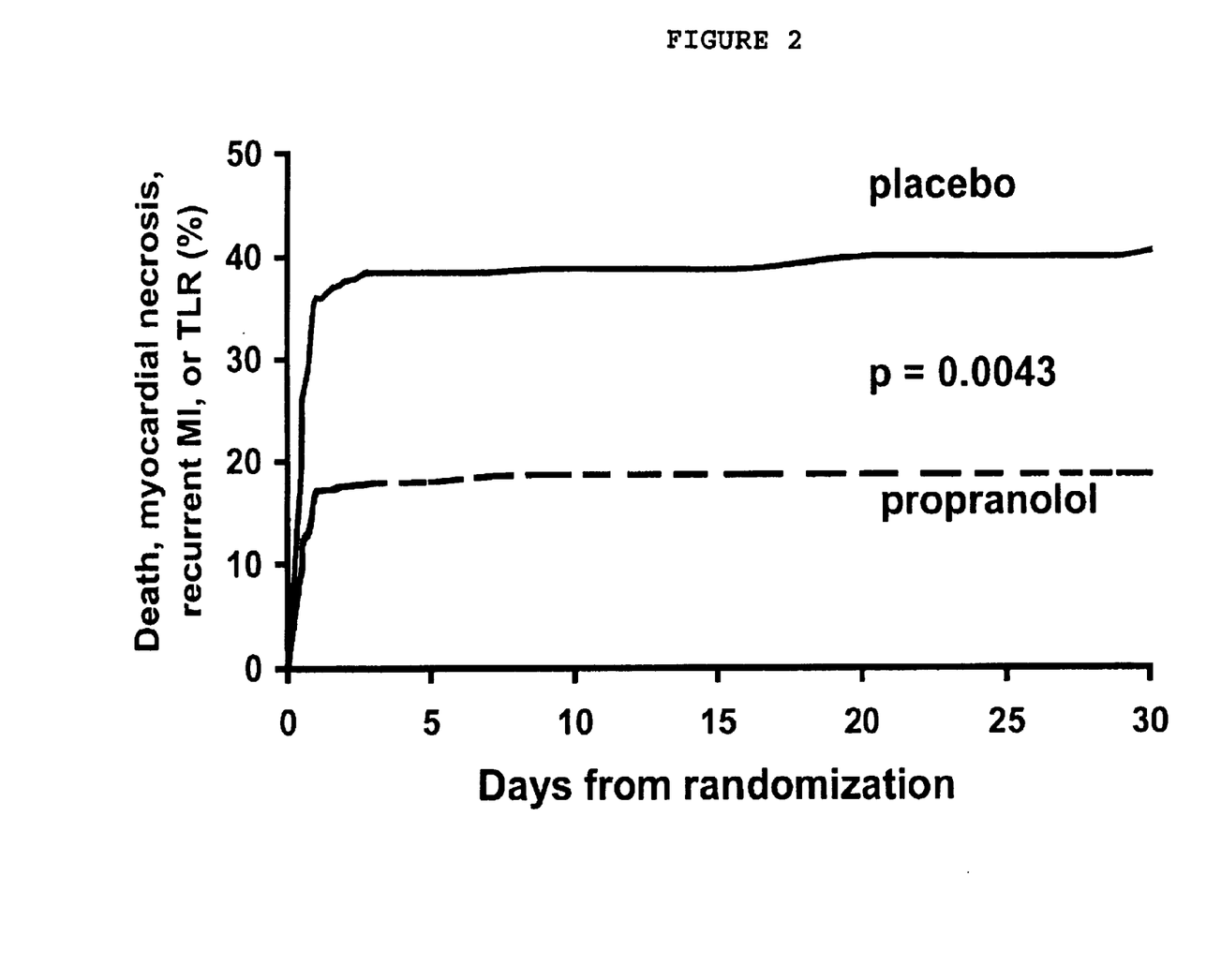
FIG. 2 is Kaplan-Meier graph showing the effect of a beta blocker, used in accordance with a method of the present invention, on subsequent clinical events.
Figure 3:
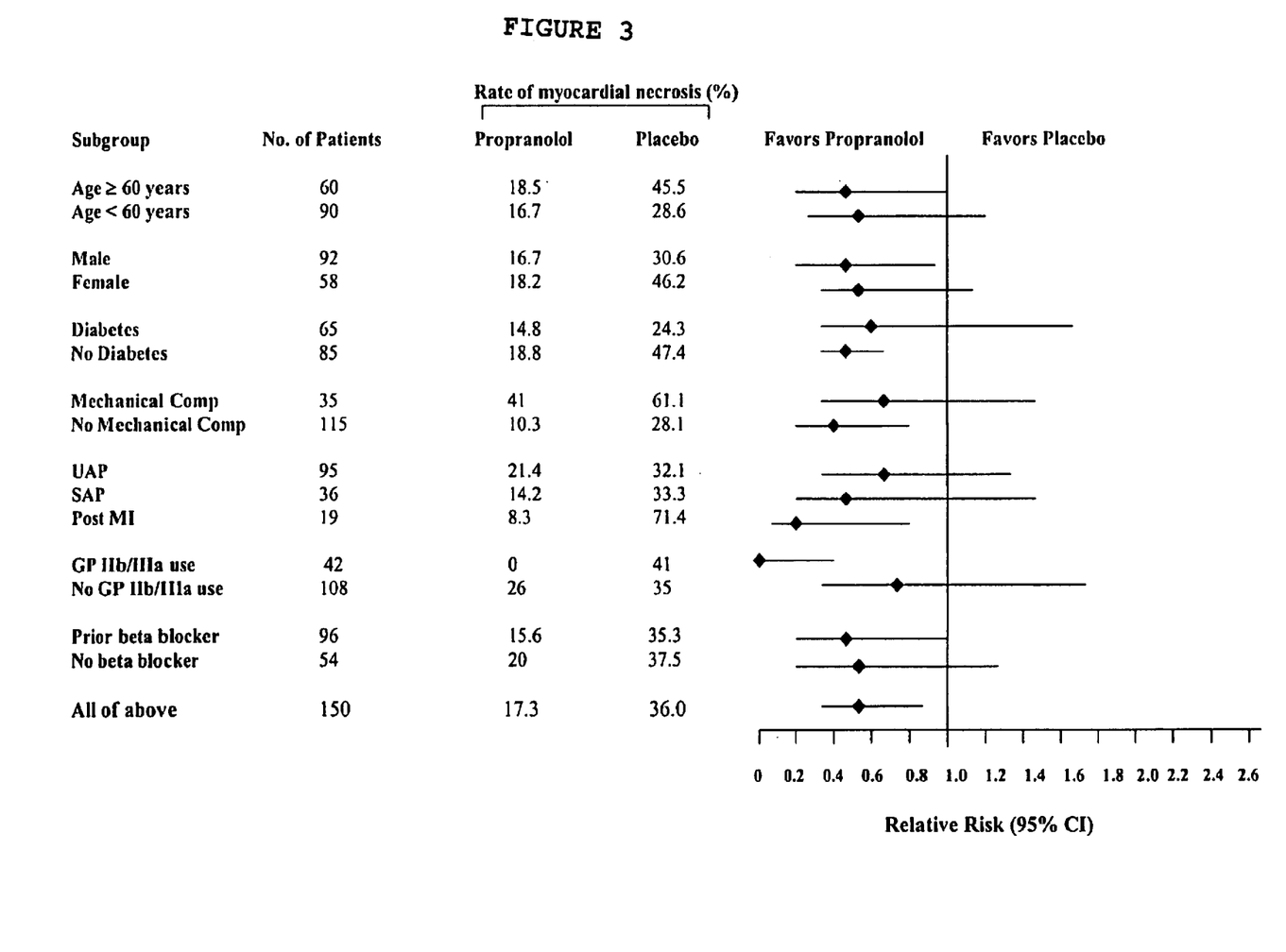
FIG. 3 is a graph showing the effect of a beta blocker, used in accordance with a method of the present invention, on relative risk of myocardial necrosis for various subgroups of subjects.
Figure 4:
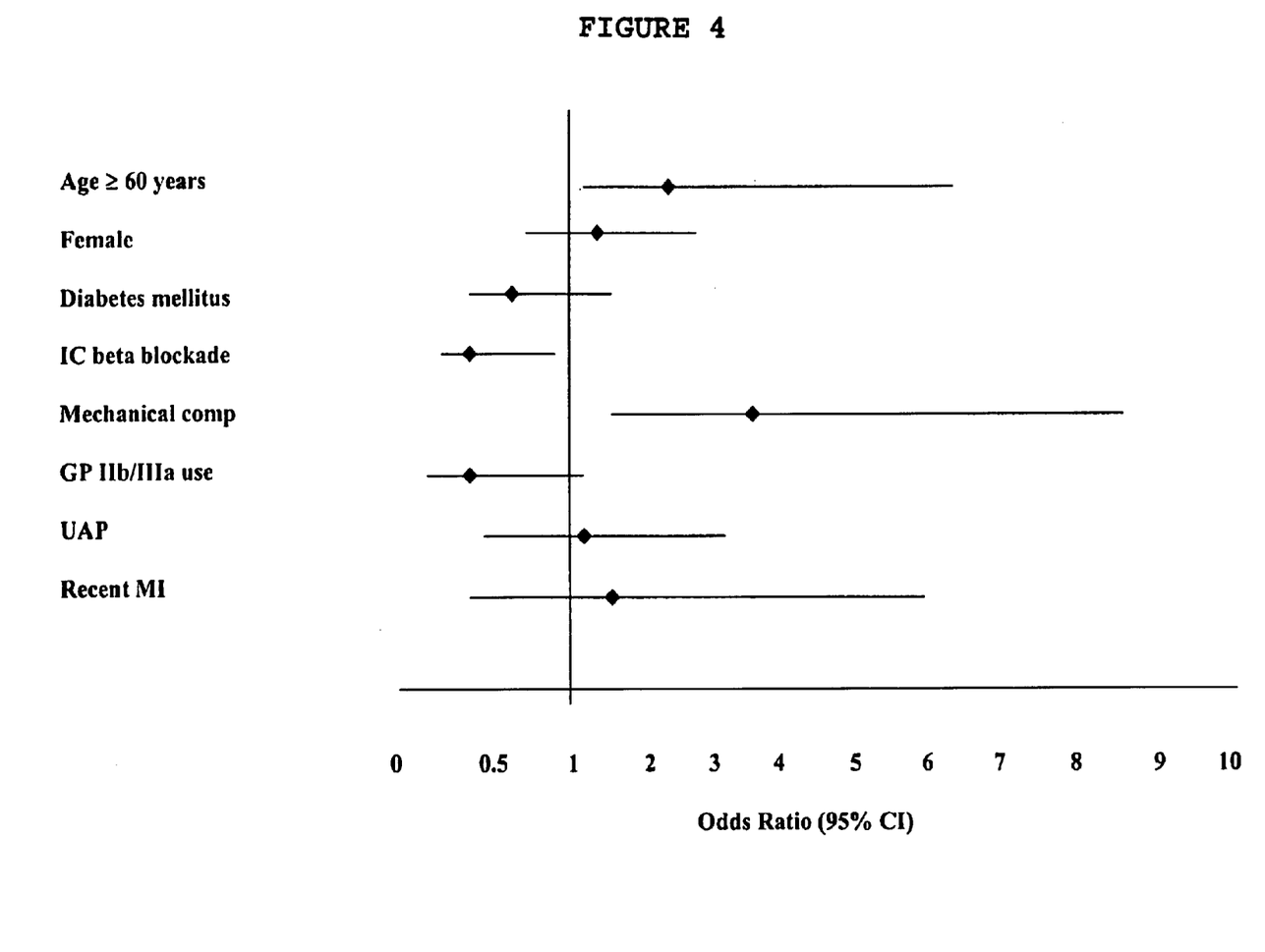
FIG. 4 is a graph showing the effect of a beta blocker, used in accordance with a method of the present invention, on CKMB elevation.

The results are discussed below with reference to FIGS. 1–4. FIG. 1 sets forth the incidence and level of CKMB, CK, and troponin T elevation post PCI in the propranolol ("Prop") and placebo groups. FIG. 2 is a Kaplan-Meier plot of cumulative event rates of the composite endpoint of death, myocardial necrosis, recurrent myocardial infarction ("MI"), and urgent TLR to 30 days after randomization according to treatment assignment. With regard to FIG. 2, it should be noted that there were 0 death, 3 recurrent MI, and 2 TLR during this period for both groups combined, and, therefore, FIG. 2 largely represents the incidence of myocardial necrosis. FIG. 3 is a graph showing the relative risk of myocardial necrosis with beta-blockade and placebo treatment by subgroups. FIG. 4 is a graph showing multivariate predictors of CKMB elevation with relative risk and 95% confidence intervals. With regard to FIG. 4, note that regional beta blockade is associated with lower risk of CKMB rise and mechanical complications are associated with increased risk of CKMB release. The following abbreviations are used in FIGS. 3 and 4: "Comp"=complication, "UAP"=unstable angina pectoris, "SAP"=stable angina pectoris, "MI"=myocardial infarction, and "GP IIb/IIIa use"=prophylactic use of GP IIb/IIIa ("rescue" use of GP IIb/IIIa not included).

Myocardial necrosis occurred significantly more frequently in the placebo than the propranolol group. An elevation of CKMB was seen in 36% of the placebo and 17% of the propranolol patients (p=0.01). Elevation of troponin T occurred in 33% of the placebo and 13% of the propranolol patients (p=0.005). This is shown in Table 3 and in FIG. 1. The median value of CKMB, CK, and troponin T in the 2 groups were as follows: CKMB, placebo 2.6, propranolol 2.1; total CK, placebo 76, propranolol 67; troponin T, placebo 0.03, propranolol 0.03.

TABLE 3

Incidence (%) of biochemical markers elevation and 30 days clinical end point after PCI.

|  | Propranolol (n = 75) | Placebo (n = 75) | P value |
|---|---|---|---|
| Elevation of CKMB (>5 ng/ml) | 17 | 36 | 0.01 |
| Elevation of Troponin T (>0.10 ng/ml) | 13 | 33 | 0.005 |
| Death | 0 | 0 | NS |
| Recurrent MI | 1 | 3 | NS |
| Urgent/emergent TLR | 0 | 3 | NS |
| Combined 30d MACE | 18 | 40 | 0.004 |

MACE = major adverse clinical event;
MI = myocardial infarction;
TLR = target lesion revascularization.
* There were 63 patients in the propranolol and 69 patients in the placebo group with a normal troponin T baseline value.

Patients with mechanical complications had a higher incidence of elevated CKMB, total CK, and troponin T than patients without mechanical complications. This is shown in Table 4. Among patients without mechanical complications, there was a highly significant difference in the incidence of CKMB elevation with placebo compared with propranolol treatment (28%, placebo vs. 10%, propranolol; p=0.015). Among patients with mechanical complications (n=35), there was a trend toward a lower incidence of myocardial necrosis in the propranolol group (61%, placebo vs. 41%, propranolol; p=0.24).

TABLE 4

The relationship of biochemical marker elevation to mechanical complications and beta blocker use (% of patients with elevation on CKMB, CK, and troponin T).

|  | Mechanical complications (n = 35) | No mechanical complication (n = 115) |
|---|---|---|
| Elevation of CKMB | 51 | 19** |
| Elevation of CK | 20 | 3** |
| Elevation of troponin T | 46 | 13** |

| Propranolol | Placebo (n = 18) | Propranolol (n = 17) | Placebo (n = 57) | Propranolol (n = 58) |
|---|---|---|---|---|
| Elevation of CKMB | 61 | 41 | 28* | 10 |
| Elevation of CK | 22 | 18 | 5 | 0 |
| Elevation of troponin T | 56 | 35 | 21* | 5 |

CKMB elevation≧3 times upper limit of normal, often used as a criterion for post-PCI MI, developed in 7 propranolol patients and 6 placebo patients. Of these 13 patients, 11 (84.6%) had an associated mechanical complication during PCI. The incidence of mechanical complications was significantly greater in patients with CKMB≧3 times upper limit of normal compared with all other patients (84.6% vs. 17.5%, p<0.0001).

The 30-day composite MACE end point (FIG. 2) occurred in 40% of placebo and in 18% of propranolol patients (p=0.004). This difference was due almost exclusively to the difference in myocardial necrosis. There were 0 deaths. Recurrent MI occurred in 3 patients (placebo 2, propranolol 1). Urgent TLR was required in 2 patients (placebo 2, propranolol 0). "Rescue" GP IIb/IIIa inhibitors use was required in 15% of placebo and 11% of propranolol groups (p=0.46). Significant bleeding occurred in 3% each of placebo and propranolol patients.

Subgroup analysis demonstrated that the favorable effect of propranolol on preventing myocardial necrosis was broadly applicable (FIG. 3).

Factors associated with increased risk of CKMB elevation after PCI are shown in FIG. 4. IC beta blocker therapy was associated with a decreased risk of and mechanical complications during PCI and age≧60 years an increased risk of CKMB release.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for reducing or preventing myocardial cell damage during and/or after percutaneous coronary intervention in a subject's coronary artery, said method comprising:
   instilling a beta blocker directly into the subject's coronary artery prior to percutaneous coronary intervention.

2. A method according to claim 1, wherein the coronary artery contains a blockage.

3. A method according to claim 1, wherein the coronary artery contains a blockage and wherein said instilling is carried out by delivering the beta blocker directly to the coronary artery.

4. A method according to claim 3, wherein the blockage is caused by a stenosis in the coronary artery.

5. A method according to claim 1, wherein the coronary artery contains a blockage and wherein said instilling is carried out by delivering the beta blocker directly to the coronary artery at and/or distal to the blockage.

6. A method according to claim 1, wherein the coronary artery contains a blockage and wherein said instilling is carried out by delivering the beta blocker directly to the coronary artery distal to the blockage.

7. A method according to claim 6, wherein the blockage is caused by a stenosis in the coronary artery and wherein said instilling is carried out by delivering the beta blocker directly to the coronary artery distal to the stenosis.

8. A method according to claim 7, wherein the beta blocker is delivered using a catheter whose distal tip is positioned across the stenosis.

9. A method according to claim 7, wherein the beta blocker is delivered using a dilatation catheter whose distal tip is positioned across the stenosis.

10. A method according to claim 7, wherein the beta blocker is delivered using an over-the-wire angioplasty balloon catheter whose distal tip is positioned across the stenosis.

11. A method according to claim 10, wherein the beta blocker is propranolol.

12. A method according to claim 1, wherein the beta blocker is propranolol.

13. A method according to claim 1, wherein said instilling is carried out using a dilatation catheter.

14. A method according to claim 1, wherein said instilling is carried out using an over-the-wire angioplasty balloon catheter.

15. A method according to claim 1, wherein the percutaneous coronary intervention comprises balloon angioplasty.

16. A method according to claim 1, wherein the percutaneous coronary intervention comprises stenting and or atherectomy.

17. A method according to claim 1, wherein the percutaneous coronary intervention comprises stenting and or atherectomy but does not involve temporarily occluding the coronary artery.

18. A method according to claim 1, wherein said instilling is carried out under conditions which are effective to inhibit the release of enzyme creatine kinase, myocardial specific enzyme CKMB, myocardial cell protein troponin I, myocardial cell protein troponin T, or combinations thereof.

* * * * *